(12) United States Patent
Matsumoto et al.

(10) Patent No.: US 12,383,233 B2
(45) Date of Patent: Aug. 12, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventors: Tsuyoshi Matsumoto, Tokyo (JP); Takahide Terada, Tokyo (JP); Tomoki Inoue, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/747,360

(22) Filed: Jun. 18, 2024

(65) Prior Publication Data

US 2024/0415492 A1 Dec. 19, 2024

(30) Foreign Application Priority Data

Jun. 19, 2023 (JP) ................... 2023-099961

(51) Int. Cl.
*A61B 8/00* (2006.01)
*A61B 8/08* (2006.01)
(52) U.S. Cl.
CPC ............ *A61B 8/469* (2013.01); *A61B 8/0891* (2013.01); *A61B 8/5207* (2013.01)
(58) Field of Classification Search
CPC ..... A61B 8/469; A61B 8/0891; A61B 8/5207; A61B 8/085; A61B 8/488
See application file for complete search history.

(56) References Cited

U.S. PATENT DOCUMENTS

2014/0334706 A1 11/2014 Toma et al.
2020/0129160 A1 4/2020 Ebata
2020/0178933 A1 6/2020 Imai

FOREIGN PATENT DOCUMENTS

JP 6836652 B2 3/2021

OTHER PUBLICATIONS

Extended European Search Report issued in EP 24 18 2844.1-1122 by the European Patent Office on Oct. 21, 2024 which is related to U.S. Appl. No. 18/747,360.

*Primary Examiner* — Michael J Carey
*Assistant Examiner* — Zainab Mohammed Aldarraji
(74) *Attorney, Agent, or Firm* — Studebaker Brackett PLLC

(57) ABSTRACT

There are provided an ultrasound diagnostic apparatus and a control method of the ultrasound diagnostic apparatus which allow a user to intuitively and easily correct a specifying result of a blood vessel region.

An ultrasound diagnostic apparatus includes a blood vessel region specifying unit that specifies a blood vessel region on the basis of a score threshold value from ultrasound images of a plurality of frames acquired in a time-series manner; a monitor that displays the ultrasound image and the specified blood vessel region; an input device that accepts designation of a position and designation regarding addition or deletion of the blood vessel region by a user; a correction region setting unit that sets a correction region on the ultrasound image on the basis of the position designated by the user; and a threshold value correction unit that corrects the score threshold value according to a designation content by the user, in which the blood vessel region specifying unit performs processing of specifying the blood vessel region on the basis of the corrected score threshold value, from the ultrasound image in the correction region.

20 Claims, 11 Drawing Sheets

ULTRASOUND DIAGNOSTIC APPARATUS AND CONTROL METHOD OF ULTRASOUND DIAGNOSTIC APPARATUS

CROSS-REFERENCE TO RELATED APPLICATIONS

The present application claims priority under 35 U.S.C. § 119 to Japanese Patent Application No. 2023-099961, filed on Jun. 19, 2023. The above application is hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which specify a blood vessel of a subject from an ultrasound image.

2. Description of the Related Art

In the related art, a so-called ultrasound diagnostic apparatus has been known which captures an ultrasound image representing a tomogram of an inside of a subject. A user such as a doctor may use such an ultrasound diagnostic apparatus to observe, for example, a blood vessel region of a subject. In this case, the user usually determines which part of the ultrasound image shows the blood vessel region in the subject by checking the ultrasound image captured by the ultrasound diagnostic apparatus. However, this determination requires a certain skill level or more, a technique has been developed to automatically specify an imaging site such as a blood vessel region, as disclosed in JP6836652B so that the user can easily observe the blood vessel region.

SUMMARY OF THE INVENTION

In a case where a technique of automatically specifying a site inside the subject as disclosed in JP6836652B is used, for some reason, the blood vessel region may not be correctly specified. In this case, it is necessary to correct a specifying result of the blood vessel region, but especially in a case where the blood vessel region is not correctly specified in a plurality of frames of ultrasound images, there has been a problem in that the user requires a great deal of effort to correct the specifying result of the blood vessel region.

The present invention has been made in order to solve such a problem in the related art, and an object of the invention is to provide an ultrasound diagnostic apparatus and a control method of the ultrasound diagnostic apparatus which allow a user to intuitively and easily correct the specifying result of the blood vessel region.

According to the following configuration, the above object can be achieved.

[1] An ultrasound diagnostic apparatus comprising:
a blood vessel region specifying unit that specifies a blood vessel region on the basis of a score threshold value from ultrasound images of a plurality of frames acquired in a time-series manner;
a monitor that displays the ultrasound image and the specified blood vessel region;
an input device that accepts designation of a position and designation regarding addition or deletion of the blood vessel region by a user;
a correction region setting unit that sets a correction region on the ultrasound image on the basis of the position designated by the user; and
a threshold value correction unit that corrects the score threshold value according to a designation content regarding the addition or deletion of the blood vessel region by the user,
in which the blood vessel region specifying unit performs processing of specifying the blood vessel region on the basis of the score threshold value corrected by the threshold value correction unit, in the correction region set by the correction region setting unit.

[2] The ultrasound diagnostic apparatus according to [1], in which in a case where the designation content is the designation to add the blood vessel region, the threshold value correction unit decreases the score threshold value until the blood vessel region in the correction region is specified, and
the blood vessel region specifying unit performs the processing of specifying the blood vessel region for a next frame by carrying over the score threshold value in a case where the blood vessel region is specified.

[3] The ultrasound diagnostic apparatus according to [1], in which in a case where the designation content is the designation to delete the blood vessel region, the threshold value correction unit increases the score threshold value until the blood vessel region in the correction region is no longer specified, and
the blood vessel region specifying unit performs the processing of specifying the blood vessel region for a next frame by carrying over the score threshold value in a case where the blood vessel region is no longer specified.

[4] The ultrasound diagnostic apparatus according to [1] to [3],
in which the correction region setting unit sets the correction region in a range that surrounds the position designated by the user and that has a predetermined shape and a predetermined size.

[5] The ultrasound diagnostic apparatus according to [1] to [3],
in which the correction region setting unit sets the correction region in a range that surrounds the position designated by the user via the input device and that is designated by the user.

[6] The ultrasound diagnostic apparatus according to [2] or [4], further comprising:
a Doppler measurement unit that performs Doppler measurement,
in which in a case where the designation content is the designation to add the blood vessel region, the correction region setting unit sets the correction region in a range in which a blood flow is recognized on the basis of the Doppler measurement by the Doppler measurement unit in a vicinity of the position designated by the user.

[7] The ultrasound diagnostic apparatus according to any one of [2], [4], [5], and [6],
in which in a case where the blood vessel region is not specified even in a case where the threshold value correction unit decreases the score threshold value, the blood vessel region specifying unit specifies the blood vessel region for a next frame by carrying over the score threshold value before being decreased.

[8] The ultrasound diagnostic apparatus according to [2], [4], [5], [6], and [7], in which in a case where the blood vessel region is not specified over a predetermined number of frames, the blood vessel region specifying unit stops adding the blood vessel region.

[9] The ultrasound diagnostic apparatus according to any one of [1] to [8], further comprising:

a correction region tracking unit that tracks the correction region along with movement of the ultrasound image between frames.

[10] The ultrasound diagnostic apparatus according to any one of [1] to [8], further comprising:

a blood vessel region tracking unit that tracks the blood vessel region along with movement of the ultrasound image between frames.

[11] The ultrasound diagnostic apparatus according to any one of [1] to [10], further comprising:

a memory that stores the blood vessel region as a correction target for the score threshold value by the threshold value correction unit and a correction content.

[12] A control method of an ultrasound diagnostic apparatus, the control method comprising:

specifying a blood vessel region on the basis of a score threshold value from ultrasound images of a plurality of frames acquired in a time-series manner;

displaying the ultrasound image and the specified blood vessel region on a monitor;

accepting designation of a position and designation regarding addition or deletion of the blood vessel region by a user;

setting a correction region on the ultrasound image on the basis of the position designated by the user;

correcting the score threshold value according to a designation content regarding the addition or deletion of the blood vessel region by the user; and performing processing of specifying the blood vessel region on the basis of the corrected score threshold value, in the set correction region.

According to the present invention, the ultrasound diagnostic apparatus includes a blood vessel region specifying unit that specifies a blood vessel region on the basis of a score threshold value from ultrasound images of a plurality of frames acquired in a time-series manner; a monitor that displays the ultrasound image and the specified blood vessel region; an input device that accepts designation of a position and designation regarding addition or deletion of the blood vessel region by a user; a correction region setting unit that sets a correction region on the ultrasound image on the basis of the position designated by the user; and a threshold value correction unit that corrects the score threshold value according to a designation content regarding the addition or deletion of the blood vessel region by the user, in which the blood vessel region specifying unit performs processing of specifying the blood vessel region on the basis of the score threshold value corrected by the threshold value correction unit, from the ultrasound image in the correction region set by the correction region setting unit. Therefore, the user can intuitively and easily correct the specifying result of the blood vessel region.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
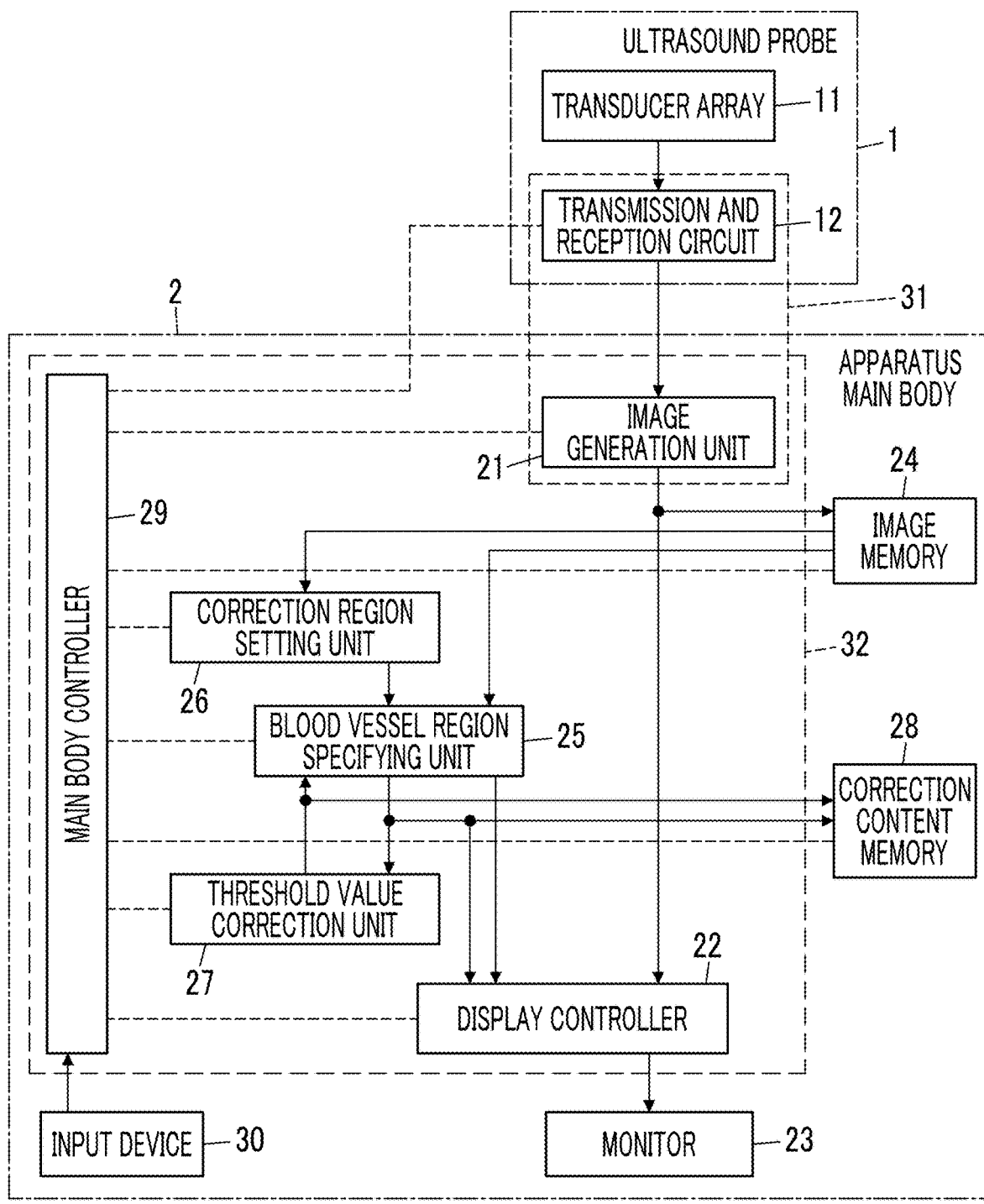
FIG. 1 is a block diagram illustrating a configuration of an ultrasound diagnostic apparatus according to a first embodiment of the present invention.

FIG. 1 illustrates a configuration of an ultrasound diagnostic apparatus according to a first embodiment of the present invention. The ultrasound diagnostic apparatus includes an ultrasound probe 1, and an apparatus main body 2 connected to the ultrasound probe 1.

The ultrasound probe 1 has a transducer array 11. A transmission and reception circuit 12 is connected to the transducer array 11.

The apparatus main body 2 has an image generation unit 21 connected to the transmission and reception circuit 12 of the ultrasound probe 1. A display controller 22 and a monitor 23 are sequentially connected to the image generation unit 21. In addition, an image memory 24 is connected to the image generation unit 21. A blood vessel region specifying unit 25 and a correction region setting unit 26 are connected to the image memory 24. The correction region setting unit 26 is connected to the blood vessel region specifying unit 25. In addition, a threshold value correction unit 27, a correction content memory 28, and the display controller 22 are connected to the blood vessel region specifying unit 25. In addition, a main body controller 29 is connected to the transmission and reception circuit 12, the image generation unit 21, the display controller 22, the image memory 24, the blood vessel region specifying unit 25, the correction region setting unit 26, the threshold value correction unit 27, and the correction content memory 28. An input device 30 is connected to the main body controller 29.

The transmission and reception circuit 12 and the image generation unit 21 constitute an image acquisition unit 31. In addition, the image generation unit 21, the display controller 22, the blood vessel region specifying unit 25, the correction region setting unit 26, the threshold value correction unit 27, and the main body controller 29 constitute a processor 32 for the apparatus main body 2.

The transducer array 11 of the ultrasound probe 1 has a plurality of ultrasonic transducers arranged in a one-dimensional or two-dimensional manner. According to a drive signal supplied from the transmission and reception circuit 12, each of the ultrasonic transducers transmits an ultrasonic wave and receives an ultrasound echo from the subject to output a signal based on the ultrasound echo. For example, each ultrasonic transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
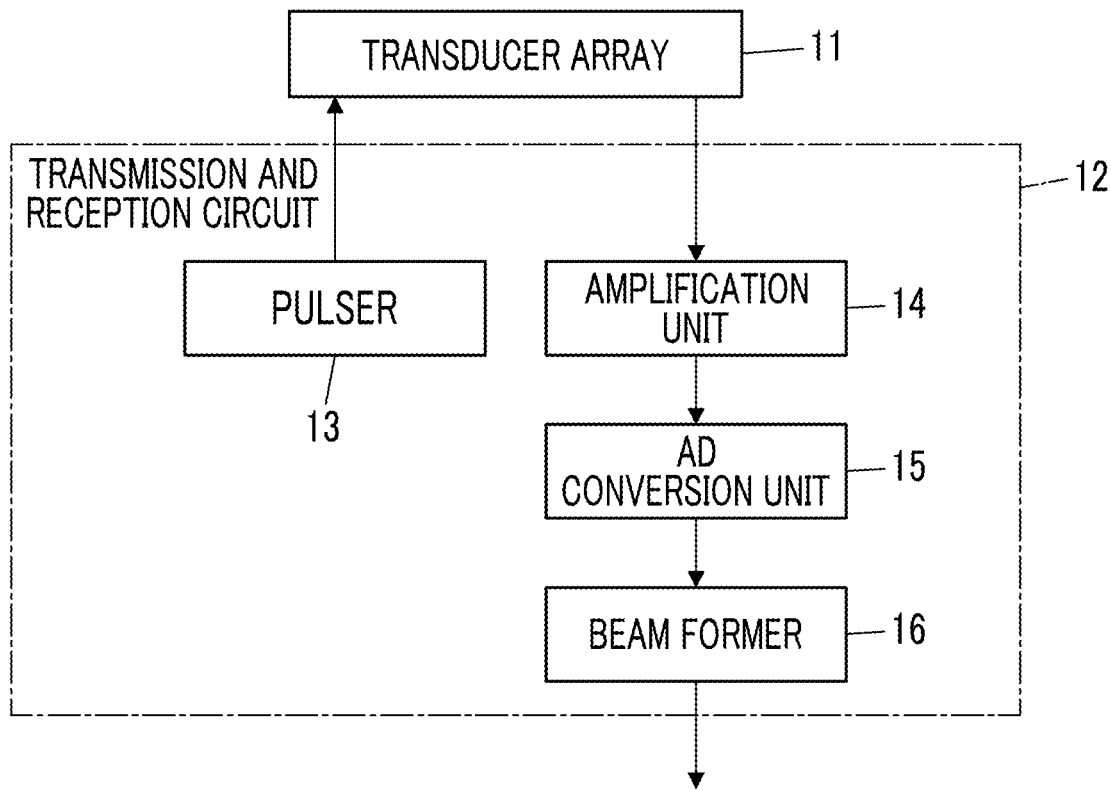
FIG. 2 is a block diagram illustrating a configuration of a transmission and reception circuit in the first embodiment of the present invention.

The transmission and reception circuit 12 causes the transducer array 11 to transmit the ultrasonic wave and generates a sound ray signal on the basis of a reception signal acquired by the transducer array 11, under the control of the main body controller 29. As illustrated in FIG. 2, the transmission and reception circuit 12 has a pulser 13 connected to the transducer array 11, and an amplification unit 14, an analog to digital (AD) conversion unit 15, and a beam former 16 that are sequentially connected in series from the transducer array 11.

The pulser 13 includes, for example, a plurality of pulse generators, and the pulser 13 adjusts the amount of delay of each drive signal so that ultrasonic waves transmitted from the plurality of ultrasonic transducers of the transducer array 11 form an ultrasound beam on the basis of a transmission delay pattern selected according to the control signal from the main body controller 29, and supplies the obtained signals to the plurality of ultrasonic transducers. Thus, in a case where a pulsed or continuous-wave voltage is applied to the electrodes of the ultrasonic transducers of the transducer array 11, the piezoelectric body expands and contracts to generate pulsed or continuous-wave ultrasonic waves from each ultrasonic transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. The ultrasound echo propagating toward the transducer array 11 in this manner is received by each ultrasonic transducer constituting the transducer array 11. In this case, each ultrasonic transducer constituting the transducer array 11 expands and contracts by receiving the propagating ultrasound echo to generate a reception signal that is an electric signal, and outputs the reception signal to the amplification unit 14.

The amplification unit 14 amplifies the signals input from each ultrasonic transducer constituting the transducer array 11, and transmits the amplified signals to the AD conversion unit 15. The AD conversion unit 15 converts the signal transmitted from the amplification unit 14 into digital reception data. The beam former 16 performs so-called reception focusing processing in which addition is performed by giving delays to respective pieces of the reception data received from the AD conversion unit 15. Through the reception focusing processing, a sound ray signal in which each piece of the reception data converted by the AD conversion unit 15 is phased and added and the focus of the ultrasound echo is narrowed is acquired.

Figure 3:
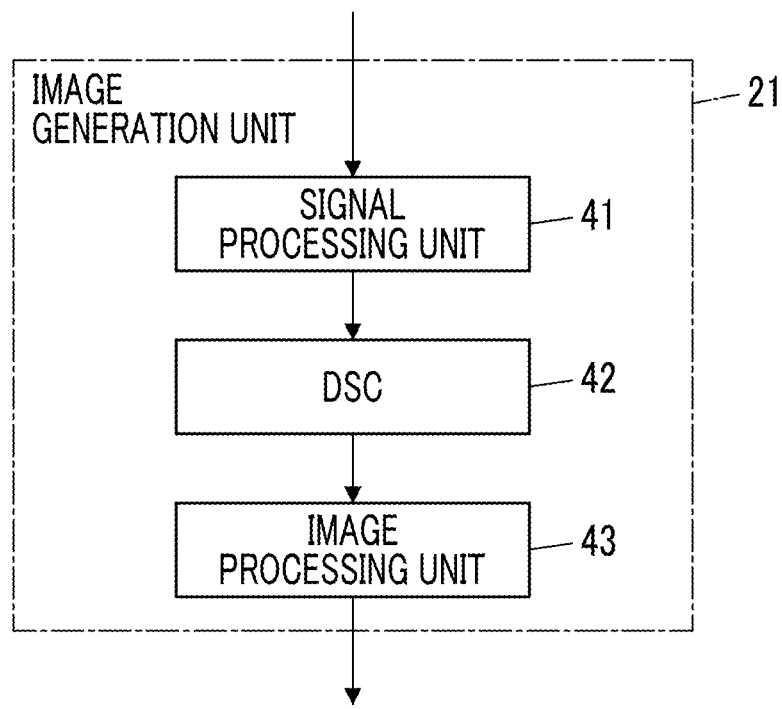
FIG. 3 is a block diagram illustrating a configuration of an image generation unit in the first embodiment of the present invention.

As illustrated in FIG. 3, the image generation unit 21 has a configuration in which a signal processing unit 41, a digital scan converter (DSC) 42, and an image processing unit 43 are sequentially connected in series.

The signal processing unit 41 generates a B-mode image signal, which is tomographic image information regarding tissues inside the subject, by performing, on the sound ray signal received from the transmission and reception circuit 12, correction of the attenuation due to the distance according to the depth of the reflection position of the ultrasonic wave using a sound speed value set by the main body controller 29 and then performing envelope detection processing.

The DSC 42 converts (raster conversion) the B-mode image signal generated by the signal processing unit 41 into an image signal according to a normal television signal scanning method.

The image processing unit 43 performs various kinds of necessary image processing such as gradation processing on the B-mode image signal input from the DSC 42, and then sends the B-mode image signal to the display controller 22. In the following, the B-mode image signal subjected to the image processing by the image processing unit 43 is simply referred to as an ultrasound image.

The display controller 22 performs predetermined processing on the ultrasound image or the like generated by the image generation unit 21 and displays the ultrasound image or the like on the monitor 23, under the control of the main body controller 29.

The monitor 23 performs various kinds of display under the control of the display controller 22. The monitor 23 can include a display device such as a liquid crystal display (LCD), or an organic electroluminescence (EL) display.

The image memory 24 is a memory that stores the ultrasound image generated by the image generation unit 21 under the control of the main body controller 29. Here, as the image memory 24, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), or a universal serial bus memory (USB memory) can be used.

The blood vessel region specifying unit 25 performs processing of reading out the ultrasound image, which is generated by the image generation unit 21 and is stored in the image memory 24, and of specifying the blood vessel region shown in the ultrasound image on the basis of a score threshold value. Here, the score threshold value is a threshold value for a score representing the blood vessel-likeness of a structure shown in the ultrasound image. The score representing the blood vessel-likeness of the structure shown in the ultrasound image can be calculated by referring to, for example, brightness information in the ultrasound image, shape information of the blood vessel-like structure shown in the ultrasound image, and arrangement information of the blood vessel-like structure shown in the ultrasound image. The arrangement information of the blood vessel-like structure shown in the ultrasound image includes information representing an arrangement relationship between the blood vessel-like structure and the anatomical structure surrounding the blood vessel-like structure.

The blood vessel region specifying unit 25 can perform processing of specifying a blood vessel region using a trained model in so-called machine learning, which is trained by a large number of ultrasound images in which the blood vessel region is shown, for example. In this case, the trained model calculates, on the basis of at least one of the brightness information, the shape information, or the arrangement information of the structure shown in the input ultrasound image, the score of the blood vessel-likeness of the structure, specifies the structure as the blood vessel in a case where the calculated score exceeds the score threshold value, and does not specify the structure as the blood vessel in a case where the calculated score is equal to or less than the score threshold value. Note that the blood vessel region specifying unit 25 can use a predetermined score threshold value as an initial value of the score threshold value.

In addition, the blood vessel region specifying unit 25 can perform processing of specifying the blood vessel using a method other than the method using the trained model. The blood vessel region specifying unit 25 can perform processing of calculating the score of the blood vessel-likeness using template matching or an image analysis technique using feature amounts such as Adaptive Boosting (Adaboost), support vector machines (SVM), and scale-invariant feature transform (SIFT), and of specifying the blood vessel on the basis of the calculated score and the score threshold value.

The input device 30 accepts an input operation of a user, and sends the input information to the main body controller 29. The user can perform designation of the position on the ultrasound image and designation regarding addition or deletion of the blood vessel region with respect to the ultrasound image on which the processing of specifying the blood vessel has been performed by the blood vessel region specifying unit 25, via the input device 30, for example.

The main body controller 29 controls each unit of the apparatus main body 2 and the ultrasound probe 1 according to a program and the like recorded in advance. The main body controller 29 can accept the designation of the position on the ultrasound image and the designation regarding addition or deletion of the blood vessel region with respect to the ultrasound image on which the processing of specifying the blood vessel has been performed by the blood vessel region specifying unit 25, by the user via the input device 30, for example.

Figure 4:
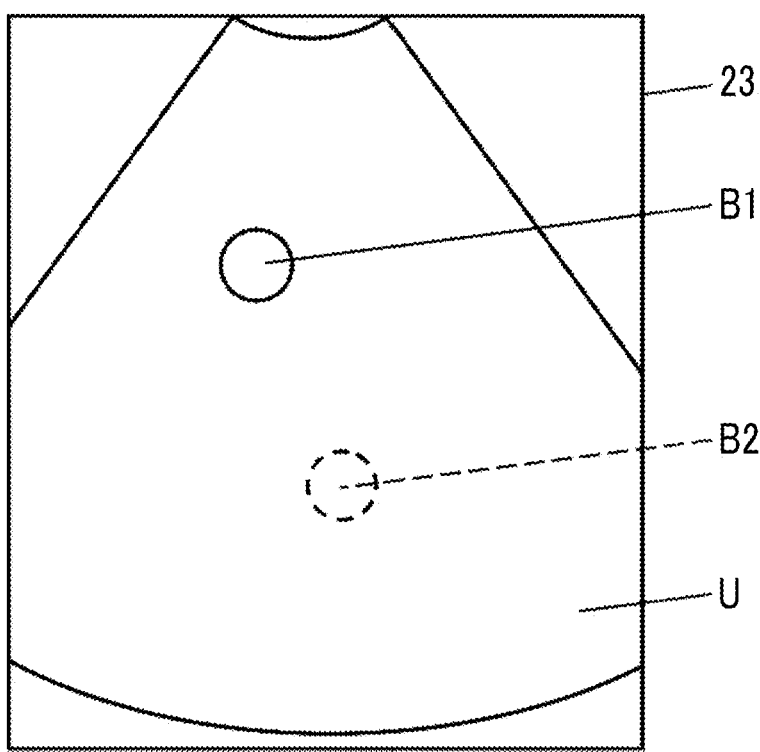
FIG. 4 is a diagram schematically illustrating an example of a blood vessel specified in the ultrasound image.
Figure 5:
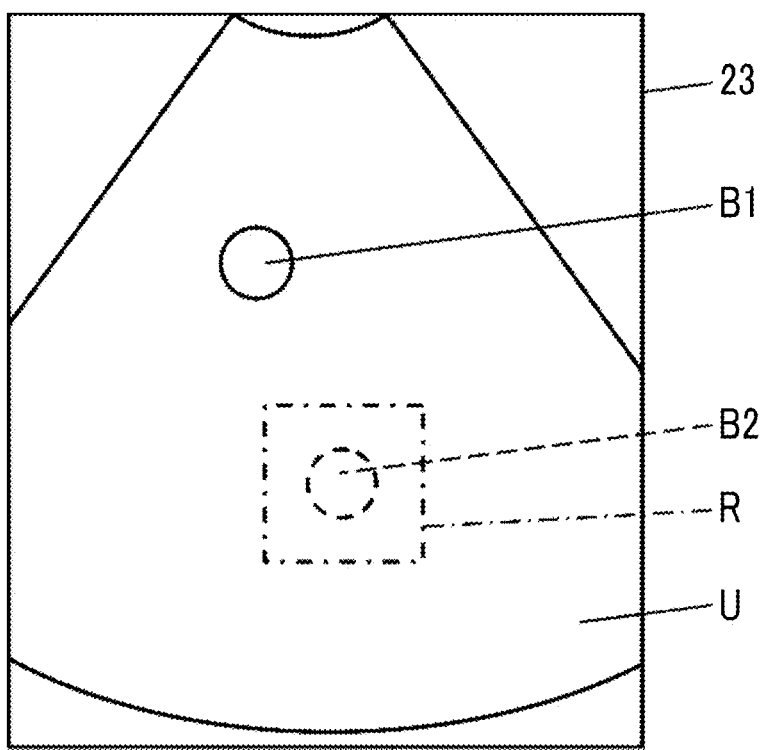
FIG. 5 is a diagram schematically illustrating an example of a set correction region.

The correction region setting unit 26 sets a correction region on the ultrasound image on the basis of the position on the ultrasound image designated by the user via the input device 30. For example, as illustrated in FIG. 4, since a blood vessel region B1 is specified but a blood vessel region B2 is not specified from the ultrasound image U by the blood vessel region specifying unit 25, in a case where the user performs designation to add the blood vessel region B2 that has not yet been specified and designates the position of the blood vessel region B2, the correction region setting unit 26 can set a correction region R surrounding the blood vessel region B2 as illustrated in FIG. 5.

Figure 6:
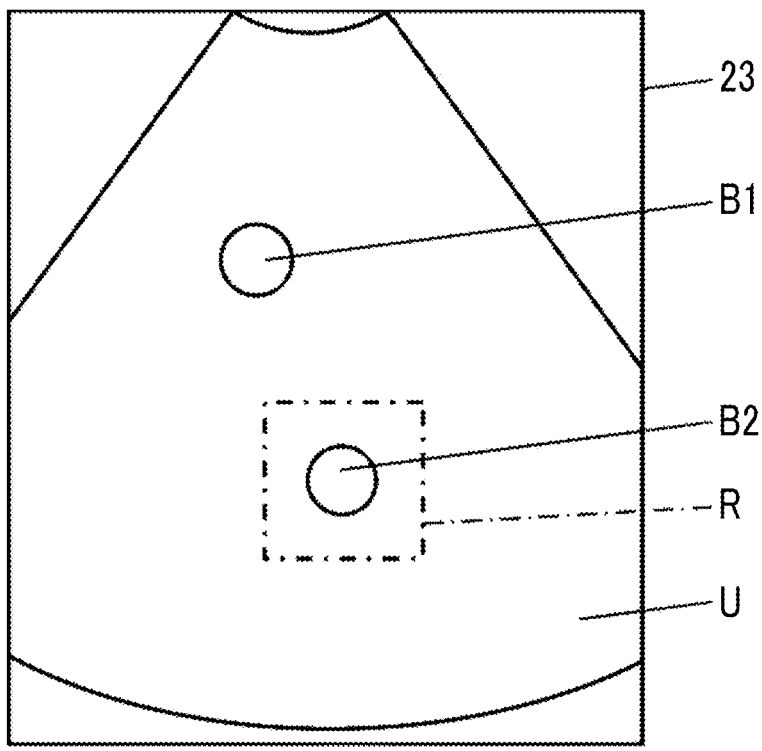
FIG. 6 is a diagram schematically illustrating another example of the set correction region.

In addition, for example, as illustrated in FIG. 6, since the blood vessel regions B1 and B2 are specified by the blood vessel region specifying unit 25 but a specifying result of the blood vessel region B2 is incorrect, in a case where the user performs designation to delete the already specified blood vessel region B2 and designates the position of the blood vessel region B2, the correction region setting unit 26 can set the correction region R surrounding the blood vessel region B2.

The correction region setting unit 26 can set the correction region R in a range that surrounds the position designated by the user and that has a predetermined shape and a predetermined size, for example. Here, the user can manually set the position on the ultrasound image U and the range surrounding the position via the input device 30, for example. In this case, the correction region setting unit 26 can set the correction region R in a range that surrounds the position designated by the user and that is designated by the user.

In addition, the correction region setting unit 26 can set the correction region R on the basis of the user's designation on the ultrasound images U of the plurality of frames which are acquired in a time-series manner by the image generation unit 21 and on which the processing of specifying the blood vessel region has been performed by the blood vessel region specifying unit 25. In this case, the correction region setting unit 26 can set the correction region R set on the ultrasound image U of one frame, also on the ultrasound images U of the other frames, for example.

The threshold value correction unit 27 corrects the score threshold value according to a designation content regarding the addition or deletion of the blood vessel region B2 by the user. The blood vessel region specifying unit 25 performs the processing of the blood vessel region B2 on the basis of the score threshold value corrected by the threshold value correction unit 27 from the ultrasound image U within the correction region R set by the correction region setting unit 26.

For example, in a case where an instruction content by the user is the designation to add the blood vessel region B2, the threshold value correction unit 27 can decrease the score threshold value until the blood vessel region is specified by the blood vessel region specifying unit 25 within the correction region R set by the correction region setting unit 26. The blood vessel region specifying unit 25 specifies the blood vessel region B2 using the score threshold value finally obtained in this manner, that is, the score threshold value in a case where the blood vessel region B2 is specified, so that the instruction content of the user to add the blood vessel region B2 to the specifying result by the blood vessel region specifying unit 25 is achieved.

For example, in a case where an instruction content by the user is the designation to delete the blood vessel region B2, the threshold value correction unit 27 can increase the score threshold value until the blood vessel region is no longer specified by the blood vessel region specifying unit 25 within the correction region R set by the correction region setting unit 26. In a case where the blood vessel region specifying unit 25 performs the processing of specifying the blood vessel region B2 using the score threshold value finally obtained in this manner, that is, the score threshold value in a case where the blood vessel region B2 is no longer specified, since the blood vessel region B2 is not specified, the instruction content of the user to delete the blood vessel region B2 to the specifying result by the blood vessel region specifying unit 25 is achieved.

In this manner, the user performs the designation regarding the addition or deletion of the blood vessel region and the designation of the position on the ultrasound image U to correct the specifying result of the blood vessel region by the blood vessel region specifying unit 25. Therefore, the user can intuitively and easily correct the specifying result of the blood vessel region by the blood vessel region specifying unit 25.

In addition, in a case where the ultrasound images U of the plurality of frames are acquired in a time-series manner by the image generation unit 21, the processing of specifying the blood vessel region is performed on the ultrasound images U of the plurality of frames by the blood vessel region specifying unit 25, and the correction region R is set on the ultrasound images U of the plurality of frames by the correction region setting unit 26, the blood vessel region specifying unit 25 can carry over the score threshold value corrected by the threshold value correction unit 27 in the ultrasound image U of one frame on which the position has been designated by the user, and perform the processing of specifying the blood vessel region in the ultrasound images U of the other frames. As a result, the specifying result of the blood vessel region designated by the user is corrected for each of the ultrasound images U of the plurality of frames.

In this manner, even in a case where the processing of specifying the blood vessel region is performed on the ultrasound images U of the plurality of frames acquired in a time-series manner, the user can intuitively and easily correct the specifying result of the blood vessel region in the ultrasound images U of the plurality of frames by performing the designation regarding the addition or deletion of the blood vessel region and the designation of the position on the ultrasound image U, on the ultrasound image U of one frame among the plurality of frames.

The correction content memory 28 is a memory that stores the blood vessel region as a correction target for the score threshold value by the threshold value correction unit 27 and the correction content under the control by the main body controller 29. As the correction content memory 28, for example, recording media such as a flash memory, an HDD, an SSD, an FD, an MO disk, an MT, a RAM, a CD, a DVD, an SD card, or a USB memory can be used.

In a case where the blood vessel region specifying unit 25 uses the trained model, the trained model can additionally learn the blood vessel region and the correction content stored in the correction content memory 28. As a result, the trained model can improve the accuracy of specifying the blood vessel region.

The processor 32 having the image generation unit 21, the display controller 22, the blood vessel region specifying unit 25, the correction region setting unit 26, the threshold value correction unit 27, and the main body controller 29 is configured by a central processing unit (CPU) and a control program for causing the CPU to execute various kinds of processing, but the processor 32 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the image generation unit 21, the display controller 22, the blood vessel region specifying unit 25, the correction region setting unit 26, the threshold value correction unit 27, and the main body controller 29 of the processor 32 can also be configured by being integrated partially or entirely into one CPU or the like.

Next, an example of the operation of the ultrasound diagnostic apparatus according to the first embodiment will be described using the flowchart illustrated in FIG. 7.

First, in Step S1, the ultrasound probe 1 is disposed on the abdomen of the subject by the user, and the ultrasound image U is acquired by the image acquisition unit 31. In this case, the reception signals are generated by the transducer array 11 of the ultrasound probe 1 transmitting the ultrasound beams into the subject and receiving the ultrasound echoes from the subject. The transmission and reception circuit 12 of the image acquisition unit 31 performs so-called reception focusing processing on the reception signals to generate sound ray signals, under the control of the main body controller 29. The sound ray signals generated by the transmission and reception circuit 12 are sent to the image generation unit 21. The image generation unit 21 generates the ultrasound image U using the sound ray signals sent from the transmission and reception circuit 12. The ultrasound image U generated here is sent to the display controller 22, and is displayed on the monitor 23.

In Step S2, the image memory 24 stores the ultrasound image U acquired in Step S1 under the control of the main body controller 29.

In Step S3, the main body controller 29 determines whether to end the capturing of the ultrasound image U. The main body controller 29 determines that the capturing of the ultrasound image U is to be continued in a case where the user does not specifically perform the designation to end the capturing of the ultrasound image U via the input device 30, for example. In this case, the processing returns to Step S1, the ultrasound image U is newly acquired. Then, the processing of Step S1 and Step S2 is repeated until the main body controller 29 determines to end the capturing of the ultrasound image U, the ultrasound images U of the plurality of frames acquired in a time-series manner are stored in the image memory 24.

The main body controller 29 determines that the capturing of the ultrasound image U is to be ended in a case where the user performs the designation to end the capturing of the ultrasound image U via the input device 30, for example, and causes the transmission and reception circuit 12 and the image generation unit 21 to stop the transmission and reception of the ultrasound beams and the generation of the ultrasound image U. In this case, the processing proceeds to Step S4.

In Step S4, the blood vessel region specifying unit 25 performs processing of specifying the blood vessel region on the basis of the predetermined score threshold value, on the ultrasound images U of the plurality of frames that are stored in the image memory 24 by repeating Step S1 and Step S2. In this case, the blood vessel region specifying unit 25 can calculate the score of the structure shown in the ultrasound image U by using a machine learning method or an image analysis algorithm using feature amounts such as template matching, AdaBoost, SVM, or SIFT, and perform processing of specifying the blood vessel region using the calculated score and the score threshold value. As a result, for example, as illustrated in FIG. 4, the blood vessel region B1 is specified on the ultrasound images U of the plurality of frames.

In Step S5, the display controller 22 displays the ultrasound image U of one frame among the ultrasound images U of the plurality of frames stored in the image memory 24, on the monitor 23. In this case, the display controller 22 displays the ultrasound image U of one frame selected by the user via, for example, the input device 30 on the monitor 23.

In Step S6, the main body controller 29 accepts the designation of the position designated by the user via input device 30 and the designation regarding the addition or deletion of the blood vessel region on the ultrasound image U displayed on the monitor 23 in Step S5.

In Step S7, the correction region setting unit 26 sets the correction region R on the ultrasound image U on the basis of the position designated by the user in Step S6. For example, in a case where the designation content of the user is a content to add the blood vessel region B2, which is not specified in Step S4, to the specifying result of the blood vessel region specifying unit 25, the correction region setting unit 26 can set the correction region R surrounding the blood vessel region B2 that has not been specified yet as illustrated in FIG. 5, on the basis of the position designated by the user. For example, in a case where the designation content of the user is a content to delete the blood vessel region B2, which has been specified in Step S4, from the specifying result of the blood vessel region specifying unit 25, the correction region setting unit 26 can set the correction region R surrounding the blood vessel region B2 that has already been specified as illustrated in FIG. 6, on the basis of the position designated by the user.

In Step S8, the threshold value correction unit 27 corrects the score threshold value that is used in the processing of specifying the blood vessel region in the correction region R set in Step S7, according to the content regarding the addition or deletion of the blood vessel region designated by the user in Step S6.

Figure 8:
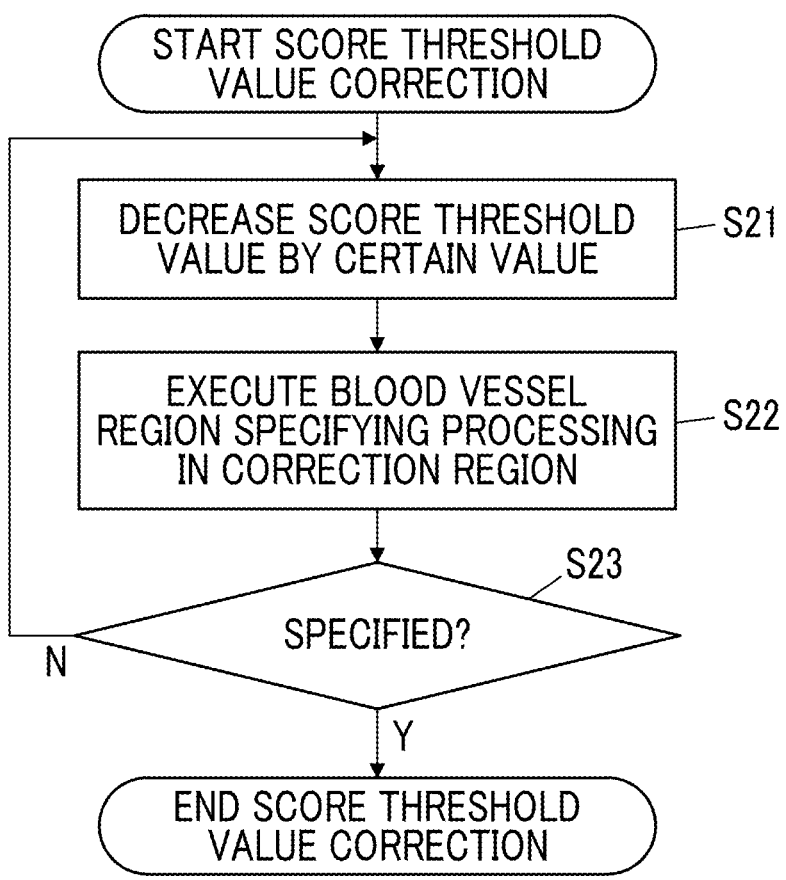
FIG. 8 is a flowchart illustrating an operation of correcting a score threshold value in the first embodiment of the present invention.

For example, in a case where the designation content in Step S6 is the designation to add the blood vessel region B2, the threshold value correction unit 27 can decrease the score threshold value until the blood vessel region B2 in the correction region R is specified. In this case, the score threshold value is corrected as in the flowchart illustrated in FIG. 8, for example.

First, in Step S21, the threshold value correction unit 27 performs processing of decreasing the current score threshold value by a certain value.

Next, in Step S22, the blood vessel region specifying unit 25 performs processing of specifying the blood vessel region B2 by using the score threshold value that has been decreased by the certain value in Step S21, in the correction region R set in Step S7.

Next, in Step S23, the threshold value correction unit 27 determines whether or not the blood vessel region B2 is specified in Step S22. Here, in a case where it is determined that the blood vessel region B2 is not specified, the threshold value correction unit 27 returns to Step S21 to perform processing of further decreasing the score threshold value by the certain value.

Then, in Step S22, the blood vessel region specifying unit 25 performs processing of specifying the blood vessel region B2 on the basis of the score threshold value that is obtained in previous Step S21 in the correction region R, and in Step S23, the threshold value correction unit 27 determines whether or not the blood vessel region B2 is specified.

In this manner, the processing of Steps S21 to S23 is repeated until it is determined in Step S23 that the blood vessel region B2 is specified. In a case where it is determined in Step S23 that the blood vessel region B2 is specified, the score threshold value obtained in the latest Step S21 is decided as the finally corrected score threshold value. As a result, the score threshold value is corrected such that the blood vessel region B2 can be specified in the correction region R.

Figure 9:
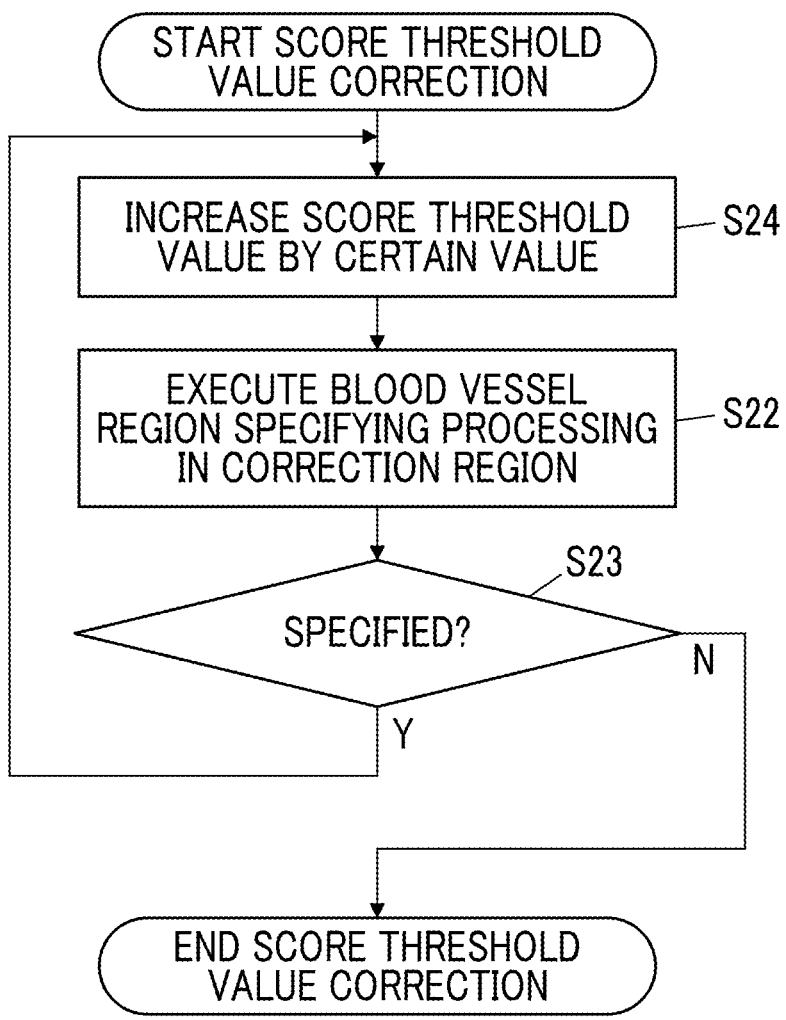
FIG. 9 is a flowchart illustrating another operation of correcting the score threshold value in the first embodiment of the present invention.

In addition, for example, in a case where the designation content in Step S6 is the designation to delete the blood vessel region B2, the threshold value correction unit 27 can increase the score threshold value until the blood vessel region B2 in the correction region R is no longer specified. In this case, the score threshold value is corrected as in the flowchart illustrated in FIG. 9, for example.

First, in Step S24, the threshold value correction unit 27 performs processing of increasing the current score threshold value by a certain value.

Next, in Step S22, the blood vessel region specifying unit 25 performs processing of specifying the blood vessel region B2 by using the score threshold value that has been increased by the certain value in Step S24, in the correction region R set in Step S7. Next, in Step S23, the threshold value correction unit 27 determines whether or not the blood vessel region B2 is specified in Step S22. Here, in a case where it is determined that the blood vessel region B2 is specified, the threshold value correction unit 27 returns to Step S24 to perform processing of further increasing the score threshold value by the certain value.

Then, in Step S22, the blood vessel region specifying unit 25 performs processing of specifying the blood vessel region B2 on the basis of the score threshold value that is obtained in previous Step S24 in the correction region R, and in Step S23, the threshold value correction unit 27 determines whether or not the blood vessel region B2 is specified.

In this manner, the processing of Step S24, Step S22, and Step S23 is repeated until it is determined in Step S23 that the blood vessel region B2 is not specified. In a case where it is determined in Step S23 that the blood vessel region B2 is not specified, the score threshold value obtained in the latest Step S24 is decided as the finally corrected score threshold value. As a result, the score threshold value is corrected such that the blood vessel region B2 cannot be specified in the correction region R.

In Step S9 subsequent to Step S8, the blood vessel region specifying unit 25 performs processing of specifying the blood vessel region B2 in the correction region R set in Step S7. In a case where the score threshold value is corrected in Step S8 such that the blood vessel region B2 is specified, the blood vessel region B2 in the correction region R is specified in Step S9, and the blood vessel region B2 is added to the specifying result of the blood vessel region. In addition, in a case where the score threshold value is corrected in Step S8 such that the blood vessel region B2 is not specified, the blood vessel region B2 in the correction region R is not specified in Step S9, and the blood vessel region B2 is deleted from the specifying result of the blood vessel region.

In this manner, in a case where the user designates the position on the ultrasound image U and the correction content in Step S6, the correction content designated by the user is achieved by the processing of Step S7 to Step S9. Therefore, the user can intuitively and easily correct the specifying result of the blood vessel region.

In Step S10, the main body controller 29 determines whether or not there is the next ultrasound image U, that is, the ultrasound image U of which the specifying result of the blood vessel region has not been corrected, among the ultrasound images U of the plurality of frames acquired by repeating Step S1 and Step S2. Here, in a case where it is determined that there is the next ultrasound image U, the processing proceeds to Step S11.

In Step S11, the main body controller 29 changes the ultrasound image U of which the specifying result of the blood vessel region is to be corrected, to the next ultrasound image U by reading out the next ultrasound image U from the image memory 24. In the ultrasound image U, the correction content designated by the user in Step S6 has not been reflected.

In Step S12, the correction region setting unit 26 sets the correction region R that is set on the previous ultrasound image U in Step S7, on the current ultrasound image U.

In Step S13, the blood vessel region specifying unit 25 performs processing of specifying the blood vessel region B2 by using the score threshold value after being corrected in Step S8, in the correction region R set in Step S12 in the current ultrasound image U. In a case where the score threshold value is corrected in Step S8 such that the blood vessel region B2 is specified, the blood vessel region B2 in the correction region R is specified in Step S13, and the blood vessel region B2 is added to the specifying result of the blood vessel region. In addition, in a case where the score threshold value is corrected in Step S8 such that the blood vessel region B2 is not specified, the blood vessel region B2 in the correction region R is not specified in Step S13, and the blood vessel region B2 is deleted from the specifying result of the blood vessel region.

In a case where the processing of Step S13 is completed, the processing returns to Step S10, and it is determined whether or not there is the next ultrasound image U. In this manner, as long as it is determined that there is the next ultrasound image U, that is, the ultrasound image U of which the specifying result of the blood vessel region has not been corrected, among the ultrasound images U of the plurality of frames acquired by repeating Step S1 and Step S2, the processing of Step S10 to Step S13 is repeated. By repeating the processing of Step S10 to Step S13, the correction content designated by the user in Step S6 is reflected on each of the ultrasound images U of the plurality of frames.

Figure 7:
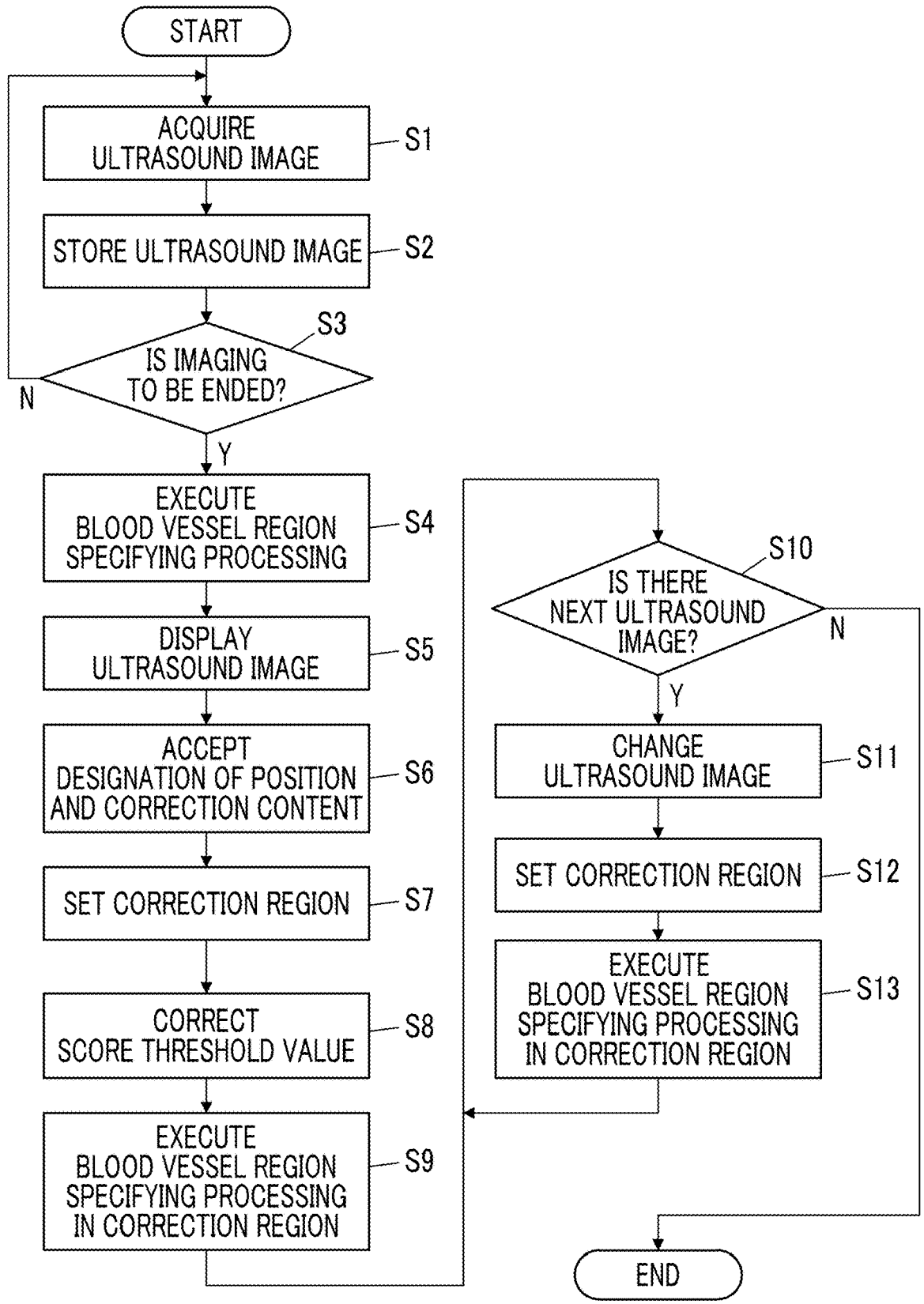
FIG. 7 is a flowchart illustrating an operation of the ultrasound diagnostic apparatus according to the first embodiment of the present invention.

In a case where it is determined in Step S10 that there is no next ultrasound image U, the operation of the ultrasound diagnostic apparatus illustrated in the flowchart of FIG. 7 is completed.

As described above, with the ultrasound diagnostic apparatus according to the first embodiment, the correction region setting unit 26 sets the correction region R on the ultrasound image U on the basis of the position designated by the user, the threshold value correction unit 27 corrects the score threshold value according to the designation content regarding the addition or deletion of the blood vessel region by the user, and the blood vessel region specifying unit 25 performs the processing of specifying the blood vessel region on the basis of the corrected score threshold value, from the ultrasound image U in the correction region R. Therefore, the user can intuitively and easily correct the specifying result of the blood vessel region.

In addition, in a case where the specifying result of the blood vessel region is corrected for the ultrasound images U of the plurality of frames acquired in a time-series manner, the user can intuitively and easily correct the specifying result of the blood vessel region in the ultrasound images U of the plurality of frames by performing the designation regarding the addition or deletion of the blood vessel region and the designation of the position on the ultrasound image U, on the ultrasound image U of one frame among the plurality of frames.

The description has been made in which the transmission and reception circuit 12 is included in the ultrasound probe 1, but the transmission and reception circuit 12 may be included in the apparatus main body 2.

In addition, the description has been made in which the image generation unit 21 is included in the apparatus main body 2, but the image generation unit 21 may be included in the ultrasound probe 1.

In addition, the apparatus main body 2 may be a so-called stationary type, a portable type that is easy to carry, or a so-called handheld type configured by a smartphone or tablet computer. As described above, the type of equipment constituting the apparatus main body 2 is not particularly limited.

In addition, the description has been made in which the ultrasound probe 1 and the apparatus main body 2 are connected to each other in a wired manner, but the ultrasound probe 1 and the apparatus main body 2 may be connected to each other in a wireless manner.

In addition, in a case where the correction for adding the blood vessel region to the specifying result of the blood vessel region in the ultrasound images U of the plurality of frames is performed and the blood vessel region is not specified even by decreasing the score threshold value by the threshold value correction unit 27, the blood vessel region specifying unit 25 can determine that there is not blood vessel region at the position designated by the user to specify the blood vessel region for the next frame by carrying over the score threshold value before being decreased, that is, the initial value of the score threshold value. As a result, in any one of the ultrasound images U of the plurality of frames, it is possible to prevent the anatomical structure other than the blood vessel region from being erroneously specified as the blood vessel region due to the decreased score threshold value, and to improve the accuracy of the specifying result of the blood vessel region.

In addition, in a case where the correction for adding the blood vessel region to the specifying result of the blood vessel region in the ultrasound images U of the plurality of frames is performed and the blood vessel region in the correction region R is not specified over a predetermined number of frames, the blood vessel region specifying unit 25 can determine that there is no blood vessel region at the position designated by the user to stop adding the blood vessel region. As a result, it is possible to prevent the blood vessel region from being erroneously added, and to improve the accuracy of the specifying result of the blood vessel region.

In addition, although not illustrated, the ultrasound diagnostic apparatus can have a correction proposal unit that proposes a correction to the specifying result of the blood vessel region on the basis of the correction content and the blood vessel region as the correction target of the score threshold value, which are stored in the correction content memory 28 in the past examination. For example, the correction proposal unit compares the blood vessel-like structure shown in the ultrasound images U of the plurality of frames where the processing of specifying the blood vessel region has been performed with the blood vessel region stored in the correction content memory 28 in the past examination, and can propose execution of correction content regarding the similar blood vessel region in a case where the blood vessel-like structure shown in the ultrasound images U of the plurality of frames is similar to the blood vessel region stored in the correction content memory 28 in the past examination. The user can improve the accuracy of the final specifying result of the blood vessel region by correcting the specifying result of the blood vessel region with reference to the proposed correction content.

In addition, the description has been made in which the blood vessel region specifying unit 25 performs the processing of specifying the blood vessel region from the entire ultrasound image U for the ultrasound images U of the plurality of frames. However, for example, in a case where the user sets a region of interest for searching for the blood vessel region for the ultrasound image U via the input device

30, the blood vessel region specifying unit 25 can specify the blood vessel region in the region of interest.

In addition, the description has been made in which the processing of specifying the blood vessel region and the processing of correcting the specifying result of the blood vessel region are performed on the ultrasound image U generated by the image generation unit 21, but the ultrasound diagnostic apparatus can perform the processing of specifying the blood vessel region and the processing of correcting the specifying result of the blood vessel region on the ultrasound image U stored in advance in the image memory 24. Here, the ultrasound image U stored in advance in the image memory 24 includes, for example, the ultrasound image U acquired in the past examination and stored in the image memory 24, and the ultrasound image U transmitted from an external device (not illustrated) and stored in the image memory 24.

In addition, the ultrasound image U stored in advance in the image memory 24 can include the ultrasound image U in which the blood vessel region has already been specified and which is stored in association with the specifying result. In this case, the ultrasound diagnostic apparatus can correct the specifying result of the blood vessel region for the ultrasound image U.

The rectangular correction region R is illustrated in FIGS. 5 and 6, but the shape of the correction region R is not limited to a rectangle. The correction region R can have a circular shape, an oval shape, a polygonal shape, or any shape, for example.

The flowchart of FIG. 7 illustrates that the processing of specifying the blood vessel region is collectively performed in Step S4 on the ultrasound images U of the plurality of frames acquired by repeating Step S1 and Step S2, but for example, the processing of specifying the blood vessel region can be performed on the ultrasound image U immediately after the ultrasound image U is acquired in Step S1. In this case, the blood vessel region specifying unit 25 can store the specifying result of the blood vessel region for the ultrasound image U of one frame in association with the ultrasound image U in the image memory 24, for example.

In addition, in the flowchart of FIG. 7, the correction region R is set for the ultrasound images U of the plurality of frames by repeating Step S10 to Step S13, but the correction region setting unit 26 can set the correction region R for all of the remaining ultrasound images U at an arbitrary timing after the correction region R is set for the ultrasound image U of the first frame in Step S7, for example.

Second Embodiment

In a case where the designation content by the user is the designation to add the blood vessel region, the correction region setting unit 26 can set the correction region R in a range where a blood flow is recognized by so-called Doppler measurement.

Figure 10:
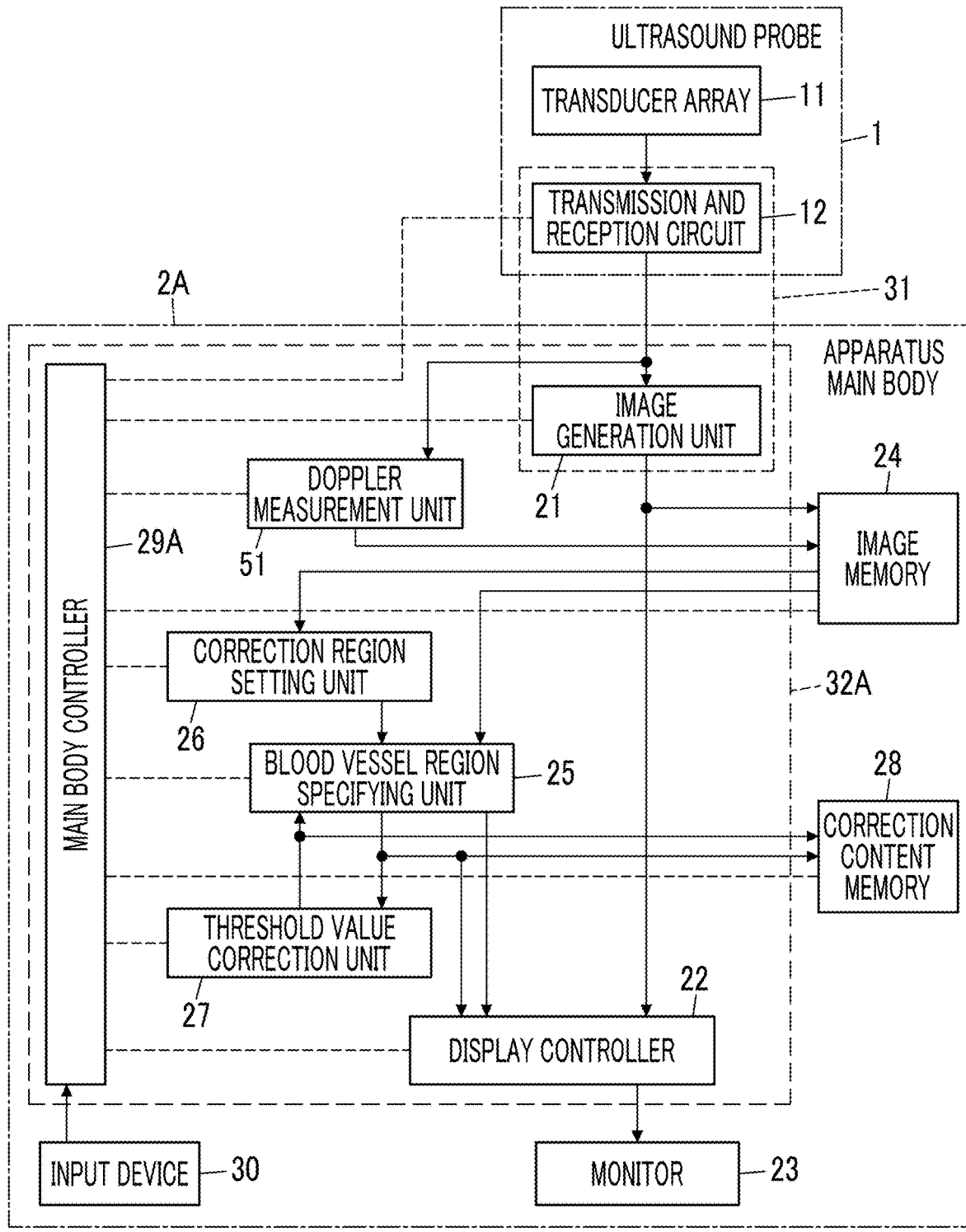
FIG. 10 is a block diagram illustrating a configuration of an ultrasound diagnostic apparatus according to a second embodiment of the present invention.

FIG. 10 illustrates a configuration of an ultrasound diagnostic apparatus of a second embodiment. The ultrasound diagnostic apparatus of the second embodiment is obtained by including an apparatus main body 2A instead of the apparatus main body 2 in the ultrasound diagnostic apparatus of the first embodiment illustrated in FIG. 1. The apparatus main body 2A is obtained by further providing a Doppler measurement unit 51 to the apparatus main body 2 in the first embodiment, and including a main body controller 29A instead of the main body controller 29.

In the apparatus main body 2A, the Doppler measurement unit 51 is connected to the transmission and reception circuit 12. The Doppler measurement unit 51 is connected to the image memory 24 and the main body controller 29A. In addition, the image generation unit 21, the display controller 22, the blood vessel region specifying unit 25, the correction region setting unit 26, the threshold value correction unit 27, the main body controller 29A, and the Doppler measurement unit 51 constitute a processor 32A for the apparatus main body 2A.

Figure 11:
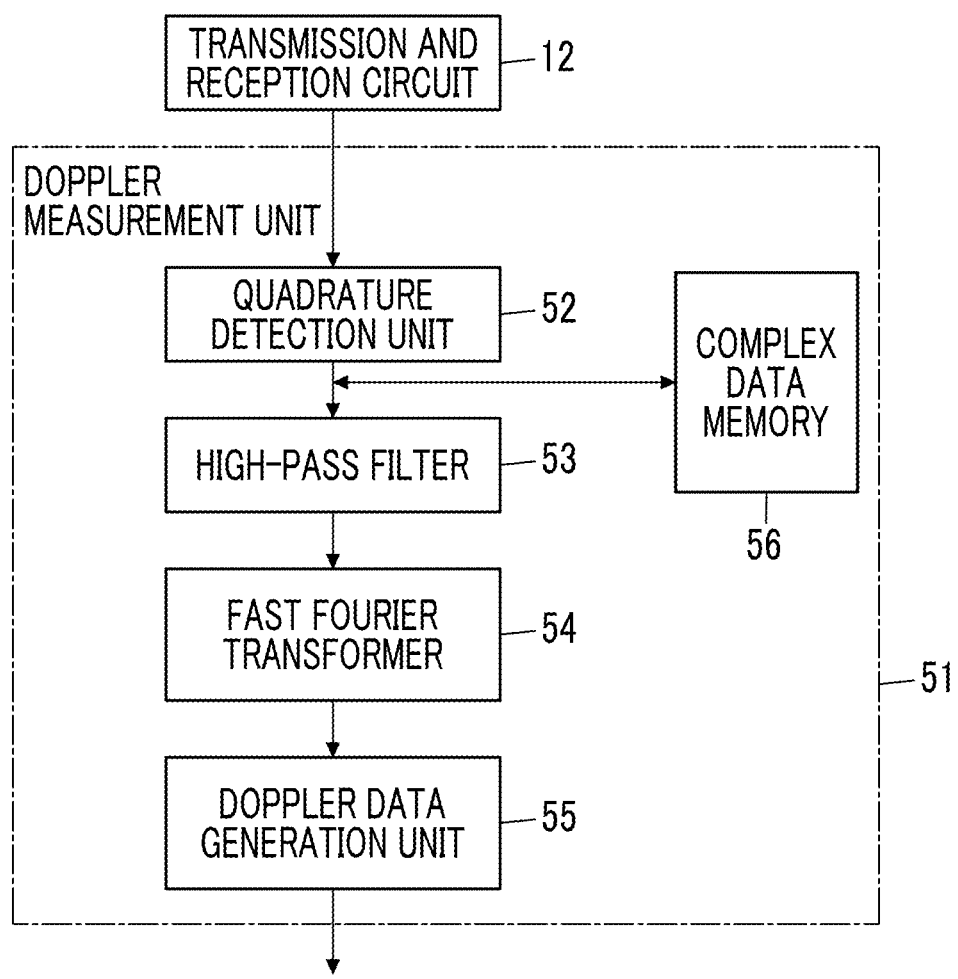
FIG. 11 is a block diagram illustrating a configuration of a Doppler measurement unit in the second embodiment of the present invention.

The Doppler measurement unit 51 is a part that performs so-called Doppler measurement, and has a quadrature detection unit 52, a high-pass filter 53, a fast Fourier transformer 54, a Doppler data generation unit 55, and a complex data memory 56 as illustrated in FIG. 11. In the Doppler measurement unit 51, the quadrature detection unit 52 is connected to the transmission and reception circuit 12, and the high-pass filter 53, the fast Fourier transformer 54, the Doppler data generation unit 55 are sequentially connected to the quadrature detection unit 52. In addition, the complex data memory 56 is connected to the quadrature detection unit 52.

The quadrature detection unit 52 mixes the sound ray signal generated by the transmission and reception circuit 12 with a carrier signal having a reference frequency to perform quadrature detection on the sound ray signal and converts the sound ray signal into complex data.

The high-pass filter 53 functions as a so-called wall filter, and removes a frequency component derived from the motion of the body tissue inside the subject, from the complex data generated by the quadrature detection unit 52.

The fast Fourier transformer 54 performs a Fourier transform on the complex data of a plurality of sample points to perform frequency analysis, obtains the blood flow velocity, and generates a spectrum signal.

The Doppler data generation unit 55 generates the Doppler data indicating the presence distribution of the blood flow in the tomographic plane of the subject corresponding to the ultrasound image U on the basis of the spectrum signal generated by the fast Fourier transformer 54.

The complex data memory 56 stores the complex data converted from the sound ray signal by the quadrature detection unit 52.

The Doppler measurement unit 51 stores the Doppler data generated in this manner in association with the ultrasound image U in the image memory 24.

In a case where the designation content by the user is the designation to add the blood vessel region, the correction region setting unit 26 can set the correction region R in a range where the blood flow is recognized on the basis of the Doppler data obtained by the Doppler measurement by the Doppler measurement unit 51 in the vicinity of the position designated by the user.

In this manner, with the ultrasound diagnostic apparatus according to the second embodiment, since the Doppler measurement unit 51 performs the Doppler measurement and the correction region setting unit 26 sets the correction region R in a range where the blood flow is recognized on the basis of the Doppler measurement by the Doppler measurement unit 51 in the vicinity of the position designated by the user, it is possible to more accurately set the correction region R at the position where the blood vessel region is present and to improve the accuracy of the specifying result of the blood vessel region.

Third Embodiment

In a case of acquiring the ultrasound images U of the plurality of frames in a time-series manner, due to the movement of the position of the ultrasound probe 1 or the like, the entire image may move in the ultrasound images U of the plurality of frames. In a case where the correction region R is set for the ultrasound images U of the plurality of frames, the ultrasound diagnostic apparatus can track the correction region R along with the movement of the ultrasound image U between frames.

Figure 12:
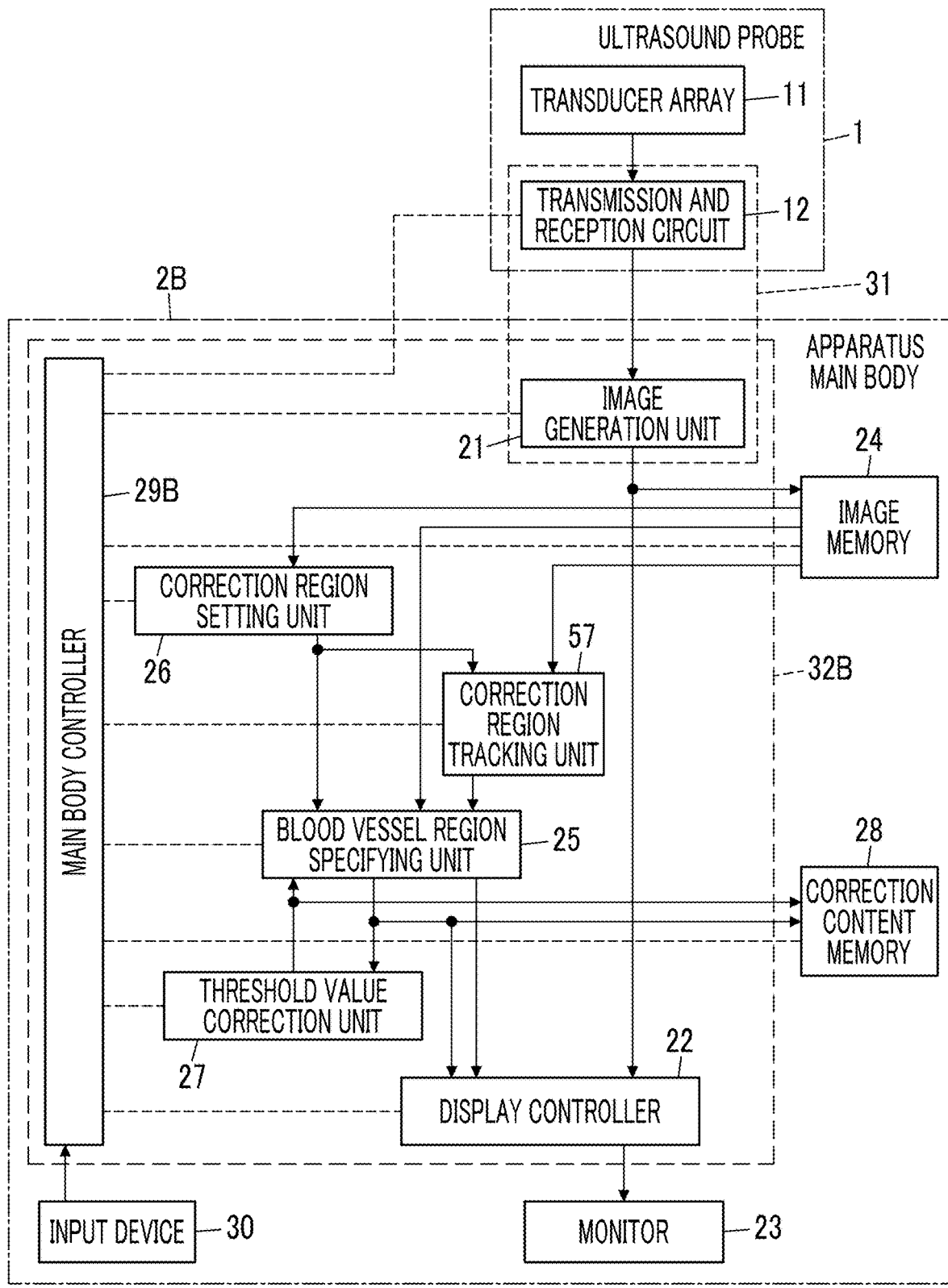
FIG. 12 is a block diagram illustrating a configuration of an ultrasound diagnostic apparatus according to a third embodiment of the present invention.

FIG. 12 illustrates a configuration of an ultrasound diagnostic apparatus of a third embodiment. The ultrasound diagnostic apparatus of the third embodiment is obtained by including an apparatus main body 2B instead of the apparatus main body 2 in the ultrasound diagnostic apparatus of the first embodiment illustrated in FIG. 1. The apparatus main body 2B is obtained by further providing a correction region tracking unit 57 to the apparatus main body 2 in the first embodiment, and including a main body controller 29B instead of the main body controller 29.

In the apparatus main body 2B, the correction region tracking unit 57 is connected to the image memory 24 and the correction region setting unit 26. The correction region tracking unit 57 is connected to the blood vessel region specifying unit 25 and the main body controller 29B. In addition, the image generation unit 21, the display controller 22, the blood vessel region specifying unit 25, the correction region setting unit 26, the threshold value correction unit 27, the main body controller 29B, and the correction region tracking unit 57 constitute a processor 32B for the apparatus main body 2B.

In a case where the correction region R is set for the ultrasound images U of the plurality of frames, the correction region tracking unit 57 tracks the correction region R initially set by the correction region setting unit 26, along with the movement of the ultrasound image U between frames caused by the movement or the like of the ultrasound probe 1 in a case of acquiring the ultrasound images U of the plurality of frames, and thereby sets the correction region R for the ultrasound images U of the remaining frames.

For example, the correction region tracking unit 57 can track the correction region R by calculating a movement amount and a movement direction of the entire image from the difference of the ultrasound image U between the frames using an algorithm such as a so-called optical flow and moving the correction region R between the frames by the calculated movement amount along the calculated movement direction. The correction region tracking unit 57 can set the correction region R in the ultrasound images U of the remaining frames by sequentially tracking the correction region R set in the ultrasound image U of which the position is designated by the user, for the previous frame and the subsequent frame in the time series stored in the image memory 24, for example.

As described above, with the ultrasound diagnostic apparatus according to the third embodiment, since the correction region tracking unit 57 tracks the correction region R along with the movement of the ultrasound image U between the frames, it is possible to more reliably set the correction region R surrounding the structure present at the position designated by the user, and to accurately correct the specifying result of the blood vessel region for the ultrasound images U of the plurality of frames.

The description has been made in which the correction region tracking unit 57 tracks the correction region R using the optical flow, but the algorithm used for tracking the correction region R is not particularly limited thereto. For example, the correction region tracking unit 57 can search the ultrasound images U using, for example, a search region (not illustrated) having the same size and shape as the correction region R, and set the correction region R in a region having the highest similarity degree with the image in the correction region R set for the previous ultrasound image U in the time series.

In addition, the description has been made in which the correction region tracking unit 57 tracks the correction region R using the algorithm such as the optical flow, but in a case where the ultrasound diagnostic apparatus includes a sensor device that detects the movement or inclination of the ultrasound probe 1, the correction region tracking unit 57 can track the correction region R on the basis of information from the sensor. For example, as the sensor device that detects the movement or inclination of the ultrasound probe 1, a gyro sensor, an acceleration sensor, a magnetic sensor, a global positioning system (GPS) sensor, or the like can be used.

In addition, the ultrasound diagnostic apparatus according to the third embodiment has a configuration in which the correction region tracking unit 57 is added to the apparatus main body 2 in the ultrasound diagnostic apparatus according to the first embodiment, but can have a configuration in which the correction region tracking unit 57 is added to the apparatus main body 2A in the ultrasound diagnostic apparatus according to the second embodiment.

Fourth Embodiment

The description has been made in which the correction region R is tracked in the third embodiment, but the ultrasound diagnostic apparatus can track the blood vessel region in the ultrasound image U between frames.

Figure 13:
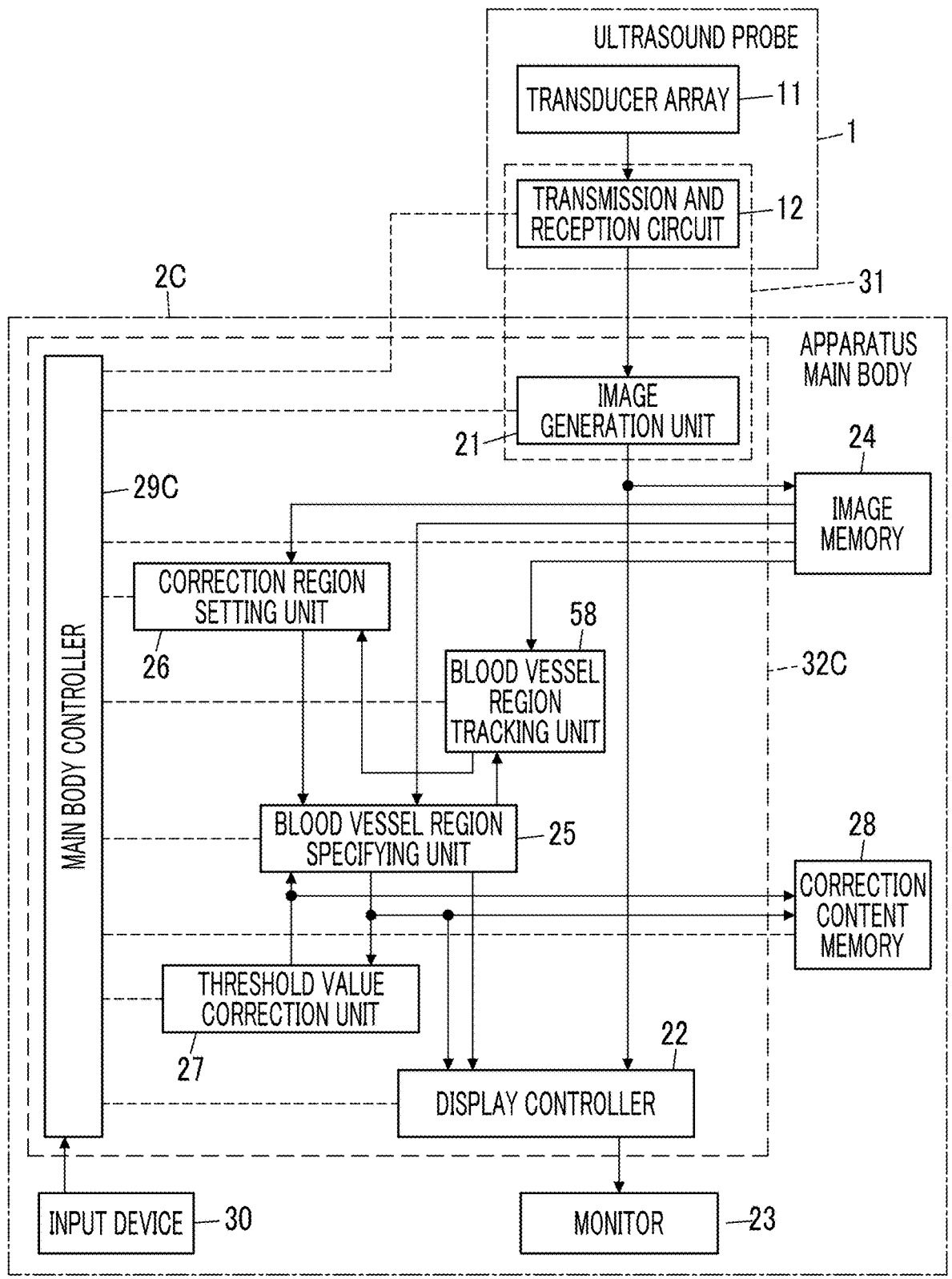
FIG. 13 is a block diagram illustrating a configuration of an ultrasound diagnostic apparatus according to a fourth embodiment of the present invention.

FIG. 13 illustrates a configuration of an ultrasound diagnostic apparatus of a fourth embodiment. The ultrasound diagnostic apparatus of the fourth embodiment is obtained by including an apparatus main body 2C instead of the apparatus main body 2 in the ultrasound diagnostic apparatus of the first embodiment illustrated in FIG. 1. The apparatus main body 2C is obtained by further providing a blood vessel region tracking unit 58 to the apparatus main body 2 in the first embodiment, and including a main body controller 29C instead of the main body controller 29.

In the apparatus main body 2C, the blood vessel region tracking unit 58 is connected to the image memory 24 and the blood vessel region specifying unit 25. The blood vessel region tracking unit 58 is connected to the correction region setting unit 26 and the main body controller 29C. In addition, the image generation unit 21, the display controller 22, the blood vessel region specifying unit 25, the correction region setting unit 26, the threshold value correction unit 27, the main body controller 29C, and the blood vessel region tracking unit 58 constitute a processor 32C for the apparatus main body 2C.

In a case where the correction region R is set for the ultrasound images U of the plurality of frames, the blood vessel region tracking unit 58 tracks the blood vessel region that has already been specified by the blood vessel region specifying unit 25, along with the movement of the ultrasound image U or the movement of the blood vessel region between frames caused by the arrangement of the blood vessel in the subject or the movement of the ultrasound probe 1 in a case of acquiring the ultrasound images U of the plurality of frames.

The blood vessel region tracking unit 58 can track the blood vessel region in the ultrasound image U between the frames, for example, in the same manner as the method in which the correction region tracking unit 57 tracks the correction region R in the third embodiment. In a case where a plurality of blood vessel regions are specified in the ultrasound image U, the blood vessel region tracking unit 58 can track the plurality of blood vessel regions after assigning a unique blood vessel name to each of the plurality of blood vessel regions in order to distinguish the plurality of blood vessel regions from each other.

In a case where the designation content of the user is the content to delete the blood vessel region from the specifying result and the position of the blood vessel region as the deletion target is designated by the user, the correction region setting unit 26 sets the correction region R surrounding the blood vessel region as the deletion target tracked by the blood vessel region tracking unit 58 in the ultrasound images U of the plurality of frames.

As described above, with the ultrasound diagnostic apparatus according to the fourth embodiment, since the blood vessel region tracking unit 58 tracks the blood vessel region along with the movement of the ultrasound image U between the frames, for example, the correction region setting unit 26 can reliably set the correction region R for the blood vessel region as the deletion target even in a case where the plurality of blood vessel regions are specified in the ultrasound image U. As a result, the designation content of the user to delete the blood vessel region can be reliably reflected in the ultrasound images U of the plurality of frames.

Note that the ultrasound diagnostic apparatus according to the fourth embodiment has a configuration in which the blood vessel region tracking unit 58 is added to the apparatus main body 2 in the ultrasound diagnostic apparatus according to the first embodiment, but can have a configuration in which the blood vessel region tracking unit 58 is added to the apparatus main body 2A in the ultrasound diagnostic apparatus according to the second embodiment, and a configuration in which the blood vessel region tracking unit 58 is added to the apparatus main body 2B in the ultrasound diagnostic apparatus according to the third embodiment.

EXPLANATION OF REFERENCES

1: ultrasound probe, 2, 2A, 2B, 2C: apparatus main body, 11: transducer array, 12: transmission and reception circuit, 13: pulser, 14: amplification unit, 15: AD conversion unit, 16: beam former, 21: image generation unit, 22: display controller, 23: monitor, 24: image memory, 25: blood vessel region specifying unit, 26: correction region setting unit, 27: threshold value correction unit, 28: correction content memory, 29, 29A, 29B, 29C: main body controller, 30: input device, 31: image acquisition unit, 32, 32A, 32B, 32C: processor, 41: signal processing unit, 42: DSC, 43: image processing unit, 51: Doppler measurement unit, 52: quadrature detection unit, 53: high-pass filter, 54: fast Fourier transformer, 55: Doppler data generation unit, 56: complex data memory, 57: correction region tracking unit, 58: blood vessel region tracking unit, B1, B2: blood vessel region, R: correction region, U: ultrasound image

What is claimed is:

1. An ultrasound diagnostic apparatus comprising:
   a monitor; and
   a processor configured to
   specify a blood vessel region based on a score threshold value from ultrasound images of a plurality of frames acquired in a time-series manner,
   display the ultrasound image and the specified blood vessel region,
   accept designation of a position and designation regarding addition or deletion of the blood vessel region by a user,
   set a correction region on the ultrasound image based on the position designated by the user, and
   correct the score threshold value according to a designation content regarding the addition or deletion of the blood vessel region by the user,
   wherein the processor is configured to perform processing of specifying the blood vessel region based on the corrected score threshold value in the correction region.

2. The ultrasound diagnostic apparatus according to claim 1,
   wherein in upon accepting the designation content to add the blood vessel region, the processor is configured to
   correct the score threshold value by decreasing the score threshold value until the blood vessel region in the correction region is specified, and
   perform the processing of specifying the blood vessel region for a next frame by carrying over the corrected score threshold value when the blood vessel region is specified.

3. The ultrasound diagnostic apparatus according to claim 1,
   wherein in upon accepting the designation content to delete the blood vessel region, the processor is configured to
   correct the score threshold value by increasing the score threshold value until the blood vessel region in the correction region is no longer specified, and
   perform the processing of specifying the blood vessel region for a next frame by carrying over the corrected score threshold value when the blood vessel region is no longer specified.

4. The ultrasound diagnostic apparatus according to claim 1,
   wherein the processor is configured to set the correction region in a range that surrounds the position designated by the user and that has a predetermined shape and a predetermined size.

5. The ultrasound diagnostic apparatus according to claim 2,
   wherein the processor is configured to set the correction region in a range that surrounds the position designated by the user and that has a predetermined shape and a predetermined size.

6. The ultrasound diagnostic apparatus according to claim 3,
   wherein the processor is configured to set the correction region in a range that surrounds the position designated by the user and that has a predetermined shape and a predetermined size.

7. The ultrasound diagnostic apparatus according to claim 1,
   wherein the processor is configured to set the correction region in a range designated by the user that surrounds the position designated by the user.

8. The ultrasound diagnostic apparatus according to claim 2,
   wherein the processor is configured to set the correction region in a range designated by the user that surrounds the position designated by the user.

9. The ultrasound diagnostic apparatus according to claim 3,
   wherein the processor is configured to set the correction region in a range designated by the user that surrounds the position designated by the user.

10. The ultrasound diagnostic apparatus according to claim 2,
wherein the processor is configured to
perform Doppler measurement, and
upon accepting the designation content to add the blood vessel region,
set the correction region in a range in which a blood flow is recognized based on the Doppler measurement in a vicinity of the position designated by the user.

11. The ultrasound diagnostic apparatus according to claim 4,
wherein the processor is configured to
perform Doppler measurement, and
upon accepting the designation content to add the blood vessel region,
set the correction region in a range in which a blood flow is recognized based on the Doppler measurement in a vicinity of the position designated by the user.

12. The ultrasound diagnostic apparatus according to claim 2,
wherein upon not being able to specify the blood vessel region by decreasing the score threshold value, the processor is configured to specify the blood vessel region for a next frame by carrying over the score threshold value before being decreased.

13. The ultrasound diagnostic apparatus according to claim 4,
wherein upon not being able to specify the blood vessel region by decreasing the score threshold value, the processor is configured to specify the blood vessel region for a next frame by carrying over the score threshold value before being decreased.

14. The ultrasound diagnostic apparatus according to claim 7,
wherein upon not being able to specify the blood vessel region by decreasing the score threshold value, the processor is configured to specify the blood vessel region for a next frame by carrying over the score threshold value before being decreased.

15. The ultrasound diagnostic apparatus according to claim 2,
wherein upon not being able to specify the blood vessel region over a predetermined number of frames, the processor is configured to stop adding the blood vessel region.

16. The ultrasound diagnostic apparatus according to claim 4,
wherein upon not being able to specify the blood vessel region over a predetermined number of frames, the processor is configured to stop adding the blood vessel region.

17. The ultrasound diagnostic apparatus according to claim 1,
wherein the processor is configured to track the correction region along with movement of the ultrasound image between frames.

18. The ultrasound diagnostic apparatus according to claim 1,
wherein the processor is configured to track the blood vessel region along with movement of the ultrasound image between frames.

19. The ultrasound diagnostic apparatus according to claim 1, further comprising:
a memory configured to store the blood vessel region as a correction target for the score threshold value by the processor and a correction content.

20. A control method of an ultrasound diagnostic apparatus, the control method comprising:
specifying a blood vessel region based on a score threshold value from ultrasound images of a plurality of frames acquired in a time-series manner;
displaying the ultrasound image and the specified blood vessel region on a monitor;
accepting designation of a position and designation regarding addition or deletion of the blood vessel region by a user;
setting a correction region on the ultrasound image based on the position designated by the user;
correcting the score threshold value according to a designation content regarding the addition or deletion of the blood vessel region by the user; and
performing processing of specifying the blood vessel region based on the corrected score threshold value, in the set correction region.

* * * * *